United States Patent
Zhang

(10) Patent No.: US 8,293,487 B1
(45) Date of Patent: Oct. 23, 2012

(54) ZESTERN, A SIMPLE, FAST, SPECIFIC AND QUANTIFIABLE IMPROVEMENT OF IMMUNODETECTION PROCESS

(75) Inventor: Jiandi Zhang, Fairfax, VA (US)

(73) Assignees: Jiandi Zhang, Fairfax, VA (US); Dan Wang, Fairfax, VA (US)

( * ) Notice: Subject to any disclaimer, the term of this patent is extended or adjusted under 35 U.S.C. 154(b) by 0 days.

(21) Appl. No.: 13/459,192

(22) Filed: Apr. 29, 2012

Related U.S. Application Data

(60) Provisional application No. 61/583,624, filed on Jan. 6, 2012.

(51) Int. Cl.
G01N 33/53 (2006.01)
(52) U.S. Cl. .......................... 435/7.1; 436/518
(58) Field of Classification Search .................. None
See application file for complete search history.

(56) References Cited

U.S. PATENT DOCUMENTS 6,759,189 B1 * 7/2004 Meikle et al. ............ 435/4

OTHER PUBLICATIONS

Yu et al. (Biochem. Engineering Journal 2004 vol. 18, p. 169-175).*
Wang et al. (Chem Communication 2008, p. 2520-2522).*
Burnette,W.N.. "Western Blotting": Electrophoretic transfer of proteins from Sodium Dodecyl Sulfate-Polyacrylamide gels to unmodified nitrocellulose and radiographic detection with antibody and radioiodinated protein A. Analytical Biochemistry (1981) V.112, pp. 195-203.
Hawkes, R., Niday,E., Gordon, J.. A Dot-immunobinding assay for monoclonal and other antibodies. Analytical Biochemistry (1982) V. 119, pp. 142-147.
Engvall, E., Perlmann, P.. Enzyme-linked immunosorbent assay (ELISA) Quantitative assay of immunoglobulin G. Immunochemistry (1971) V. 8, pp. 871-874.
Engvall, E., Jonsson, K., Perlmann, P.. Enzyme-linked immunosorbent assay II. Quantitative assay of protein antigen, immunoglobulin G, by means of enzyme-labelled antigen and antibody-coated tubes. Biochimica et biophysica acta (1971) V. 251, pp. 427-434.
Engvall, E., Perlmann, P.. Enzyme-linked immunosorbent assay, ELISA III. Quantitation of specific antibodies by enzyme-labeled anti-immunoglobulin in antigen-coated tubes. The Journal of Immunology (1972) V. 109, pp. 129-135.
Yalow, R. S., Berson, S. A.. Immunoassay of endogenous plasma insulin in man. Journal of Clinical Investigation (1960) V. 39, pp. 1157-1175.
Zhang, J.. The direct involvement of SirT1 in insulin-induced insulin receptor substrate-2 tyrosine phosphorylation (2007) V. 282, pp. 34356-34364.

* cited by examiner

*Primary Examiner* — Jacob Cheu

(57) ABSTRACT

The present invention provides an improved, simple and quantifiable process of immunodetection with improved specificity, allowing for its large-scale applications in clinical, pharmaceutical and biomedical studies and diagnostics applications. Compared with traditional immunodetection methods, this invention eliminates gel separation and transfer steps, and the results can be directly quantified with improved specificity. This invention adds one elution step in a typical immunodetection process, where bound immunocomplex is exposed to elution solution containing excessive amount of antigen or part of antigen in single or multiple copies within one molecule, to liberate bound antibody labeled with reporter enzyme into solution for direct quantification. This invention can be particularly useful to improve both the efficiency and accuracy of Western blot, Dot blot, ELISA and protein microarray analysis in multiwell plate format. It also allows for the automation of protein analysis for clinical, pharmaceutical, and biomedical applications and their diagnostics applications.

14 Claims, 2 Drawing Sheets

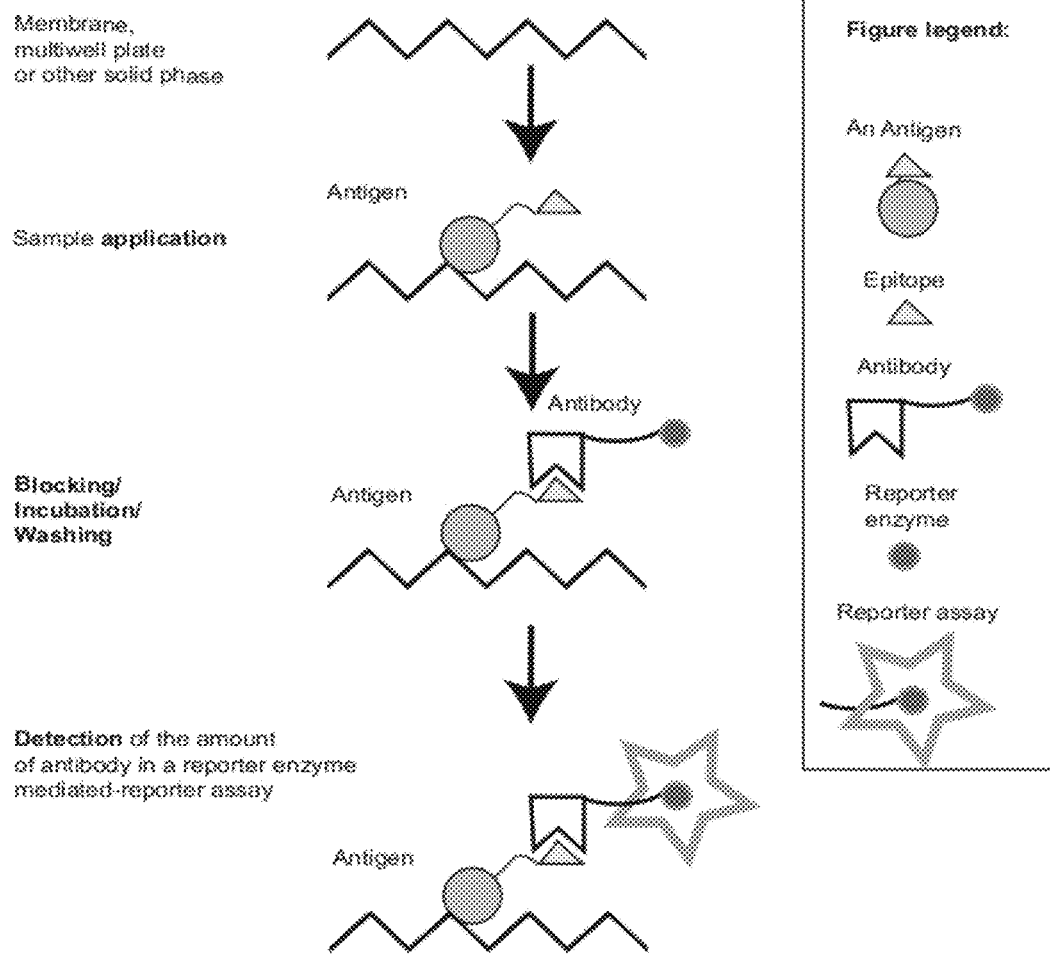
Figure 1: Conventional Immunodetection process

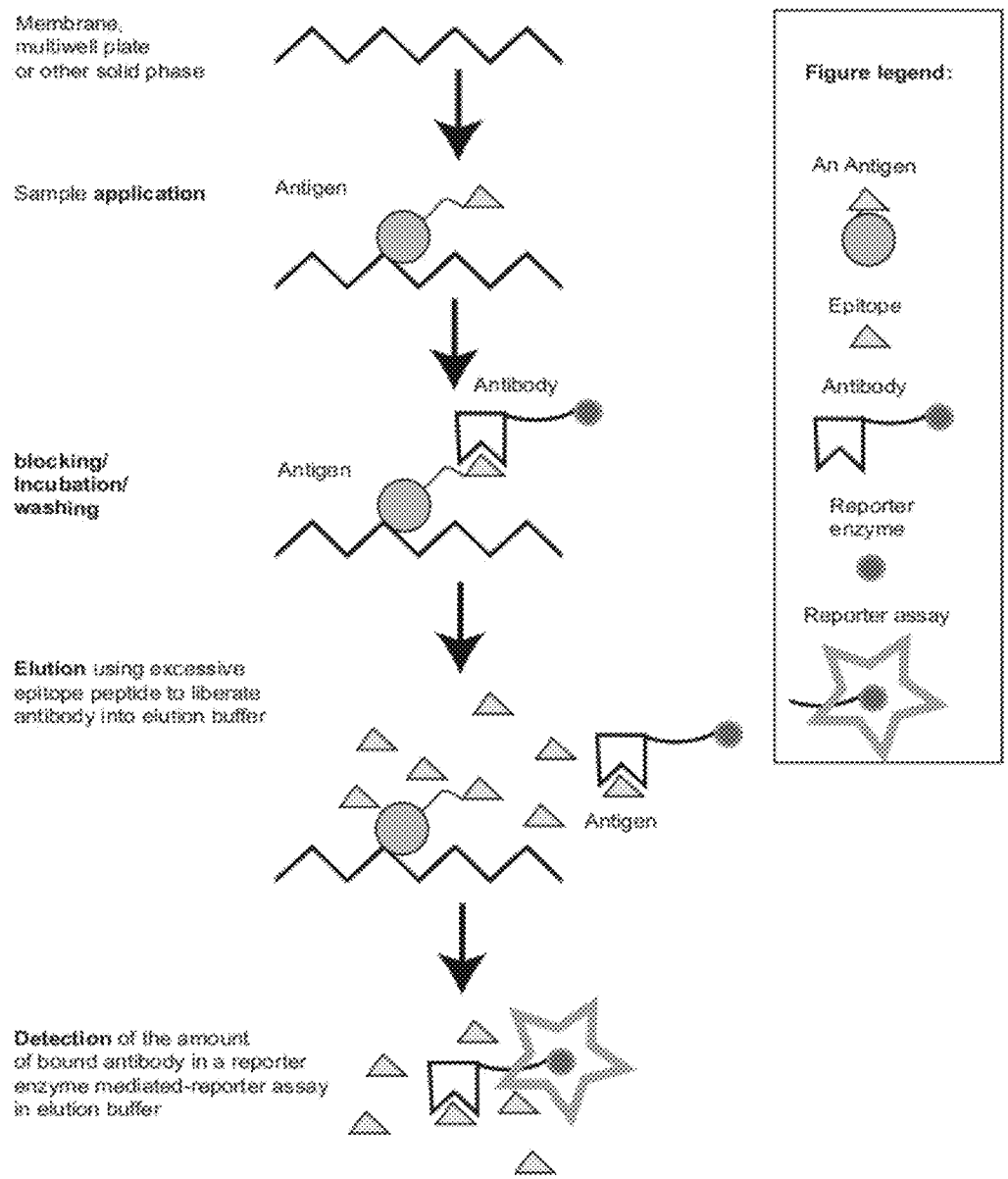
Figure 2: Zestern, the improved immunodetection process

ZESTERN, A SIMPLE, FAST, SPECIFIC AND QUANTIFIABLE IMPROVEMENT OF IMMUNODETECTION PROCESS

REFERENCES CITED

Other Publications

W. N. Burnette, "Western Blotting": Electrophoretic transfer of proteins from sodium dodecyl sulfate-polyacrylamide gels to unmodified nitrocellulose and radioiodinated protein A. Analytical Biochemistry, (1981) V. 112, pp. 195-203

R. Hawkes et al., A dot-immunobinding assay for monoclonal and other antibodies. Analytical Biochemistry. (1982) V. 119, pp. 142-147.

E. Engvall et al., Enzyme-linked immunosorbent assay (ELISA) Quantitative assay of immunoglobulin G. Immunochemistry (1971[a]) V. 8, pp. 871-874.

E. Engvall et al., Enzyme-linked immunosorbent assay II. Quantitative assay of protein antigen, immunoglobulin G, by means of enzyme-labelled antigen and antibody-coated tubes. Biochimica et Biophysica Acta (1971[b]) V. 251, pp 427-434.

E. Engvall et al., Enzyme-linked immunosorbent assay, ELISA: III. Quantitation of specific antibodies by Enzyme-labeled anti-immunoglobulin in antigen-coated tubes. The Journal of Immunology (1972), V. 109, pp 129-135.

Jiandi Zhang, The direct involvement of SirT1 in insulin-induced insulin receptor substrate-2 tyrosine phosphorylation. (2007), V. 282, pp. 34356-34364.

Yalow, R. S., Berson, S. A. Immunoassay of endogenous plasma insulin in man. Journal of Clinical Investigation (1960) V. 39, pp 1157-75.

FIELD OF INVENTION

The present invention relates to an immunodetection process for an antigen such as a chemical compound, a peptide, a protein, an RNA, a DNA, a cell (proteins released in situ), or a virus particle (proteins released in situ). In particular, this invention provides simple and improved method with quantifiable result for performing immunodetection assays including but not limited to Western blot analysis, Dot analysis, ELISA assay and their applications in multiwell plate format, and automation of protein analysis.

BACKGROUND ART

Protein analysis is the fundamental basis of modern biology research. It centers on antigen-antibody interaction to measure levels of antigen of interest under various medical or experimental conditions. An antigen by definition, is a foreign molecule that, when introduced into the body, triggers the production of an antibody by the immune system. The high specificity of the antibody against a specific antigen makes it a powerful tool in clinical, pharmaceutical and biomedical research. An antigen includes, but not limited to a chemical compound, a peptide, a protein, an RNA, a DNA, a cell (proteins released in situ), or a virus particle (proteins released in situ). The whole molecule of antigen, or part of the molecule, may be introduced into a mammal, such as a donkey, a goat, or a rabbit to generate large quantity of antibody against the introduced antigen of interest. Furthermore, the introduced antigen, or part of the antigen, may have one or several epitopes, thus may generate one or several antibodies against the antigen of interest depending on the number of epitope(s) available.

A typical immunodetection process can be divided into three major steps, including, (i), Sample application, where prepared samples containing an antigen of interest are first bound to a membrane, such as nitrocellulose or PVDF membrane or other solid phase like multiwell plate with protein binding capacity; (ii), blocking/incubation/washing step, which includes multiple sub-steps, where first (a), non-specific protein binding sites on the membrane are blocked using blocking buffer to avoid non-specific protein binding to the membrane; next (b), the membrane is incubated with antibody against antigen of interest to allow for the formation of membrane-bound antigen-antibody complex while unbound antibodies are washed away. In this sub-step, the antibody used may be directly labeled, or indirectly labeled through a secondary antibody, with a reporter enzyme such as horseradish peroxidase or alkaline phosphatase; and (iii), detection, enzymatic reaction is initiated using reporter enzyme coupled with membrane-bound antibody in a reporter assay to give a readout comprising information related to the quantity or quality of the bound immunocomplex on the membrane. For example, the readout may result in color for visual inspection or a chemiluminescence signal that can be detected either through luminometer or X-ray film. The antibody could also be fluorescence-labeled as in ELISA assay, and the final product is quantified at different wavelength in an ELISA plate reader. In both Dot blot analysis and Western blot analysis, the final result of the immunodetection analysis can be further quantified indirectly through densitometric analysis.

There are multiple modifications of this generalized procedure in each individual step. In step (i), there are variations of sample application, including direct application in Dot blot analysis, gel transfer in Western blot analysis and coating of samples in ELISA analysis. There are even more modifications in step (ii) including the various procedures and buffer compositions to maximally eliminate direct antibody binding while preserving the formed immunocomplex on the membrane. In most cases, the primary antibody is not directly labeled with reporter enzyme. A reporter enzyme coupled-secondary antibody against the primary antibody maybe needed to label those primary antibodies bound to the antigen of interest on the surface of membrane. In step (iii), there are a variety of methods to label the antibody besides reporter enzyme, leading to various detection methods accordingly.

While this generalized description of the immunodetection process is merely illustration of the principles underlying the conventional immunodetection analysis, it is by no means to exhaust all the methods or modifications associated with this process. There are always modifications or procedures not described here, yet consistent with the scope and the spirit of this generalized immunodetection process.

Dot blot analysis is a typical application of the above described immunodetection process, symbolized by the direct application of the prepared samples on to membrane in a dot. However, although this process is simple and fast, its application in biomedical, clinical and pharmaceutical research is greatly limited by its lack of specificity. In multiple cases, antibody used in immunodetection assay reacts with more than one antigen for various reasons. Therefore, the amount of the reporter enzyme associated with bound immunocomplex in a Dot blot analysis cannot reflect reliably the amount of the antigen of interest in prepared samples. Consequently, both Western blot analysis and ELISA assay are more commonly used due to improved specificity.

In Western blot analysis, prepared samples containing the antigen of interest are first separated by their molecular weight though gel electrophoresis, and the separated proteins are transferred through electroblotting step to either nitrocellulose membrane or PVDF membrane. Followed by a typical immunodetection process, the levels of the antigen of interest in the prepared samples are detected on the spot in a typical reporter enzyme-based reaction, and quantified indirectly through densitometric analysis. In this analysis, the specificity of immunodetection is achieved by both the antigen-antibody interaction as well as the expected molecular weight of the antigen of interest to eliminate any false signals due to non-specific antigen-antibody interactions commonly observed in Dot blot analysis. However, in both Dot blot analysis and Western blot analysis, the relative amount of the antigen of interest can only be quantified indirectly through densitometric analysis. Also, in Western blot analysis, the complexity of the process prevents its application in large-scale analysis in clinical, pharmaceutical and experimental research.

On the other hand, ELISA assay successfully avoids problems associated with both Dot blot analysis and Western blot analysis to allow fast, simple and quantifiable results in a multiwell plate format. The specificity of the assay is achieved by selecting antibody exclusively reacting with the antigen of interest. The high specificity of the antibody-antigen reaction also allows for direct quantification of signal intensity in multiwell plate format. These advantages lead to the wide usage of ELISA techniques in both biomedical and clinical research. Yet, the success of ELISA assay demands high specificity of the antibody, and only those reacting exclusively to the antigen of interest are acceptable for further development. This limitation leads to high developmental cost of successful ELISA assay and limits its availability in the field of biomedical research.

In this invention, an improved immunodetection process on the basis of Dot blot analysis is disclosed to circumvent the limitations associated with current available immunoassay techniques, with the distinct advantage of being simple, fast, directly quantifiable, specific, and suitable for large scale applications in clinical, pharmaceutical and experimental research and diagnostic applications. As this invention is believed to be the ultimate form of "Western" blot analysis, this invention is named "Zestern" analysis, as Z is the last letter of alphabet.

BRIEF SUMMARY OF THE INVENTION

The present invention provides a method to eliminate gel electrophoresis and blot transfer steps in Western blot analysis, and to improve the specificity of the Dot blot assay by including an elution step in otherwise a typical immunodetection process. This additional step allows membrane-bound antigen-antibody immunocomplex, where the antibody is labeled directly or indirectly with reporter enzyme, to expose to a solution containing excessive amount of antigen (or part of antigen in single or multiple copies within a single molecule). The excessive amount of antigen in the elution solution leads to the liberation of labeled antibody from bound immunocomplex into elution solution, allowing for direct quantification of the amount of reporter enzyme liberated from membrane as an indication of the amount of the antigen of interest in prepared samples.

This added elution step increases the assay specificity, as only antibody bound to the antigen of interest can be displaced from the bound immunocomplex by excessive amount of antigen. Compared with both Dot blot analysis and Western blot analysis, it also allows direct quantification of the result of the immunodetection analysis in solution and in its multiwell plate format, a feature highly desired in today's clinical and pharmaceutical studies and diagnostic applications. In addition, it also reduces the cost and efforts commonly associated with ELISA assay development to increase its availability in clinical, pharmaceutical and biomedical research and its diagnostic applications. Furthermore, it provides basis for protein array analysis and automation of the protein analysis process in clinical, biopharmaceutical and experimental research and their diagnostic applications.

BRIEF DESCRIPTION OF DRAWINGS

FIG. 1. Generalized illustration of conventional immunodetection process.

FIG. 2: Generalized illustration of Zestern, the improved immunodetection process.

DETAILED DESCRIPTION OF THE INVENTION

Unless defined otherwise, all technical and scientific terms used herein have the same meaning as is commonly understood by one of skills in the art to which this invention belongs. All publications and patents referred to herein are incorporated by reference.

The invention provides methods useful for performing antigen or antibody detection or diagnostics using Western blots (Burnette, W. N., 1981), Dot blots (Hawkes, R et al, 1982) and ELISA analysis (Engvall E. et al, $1971^a$, $1971^b$, and 1972) The invention provides a significant improvement of the conventional Western blot, Dot blot, and ELISA techniques to allow for simple, fast, specific and quantifiable result of immunological analysis of the antigen of interest in prepared samples, allowing large scale analysis of antigen of interest in clinical, pharmaceutical and biomedical research.

Conventional immunodetection analysis, as described in the background art, can be summarized into three parts, as demonstrated in FIG. 1. Those skilled in the art will know how to prepare samples for immunodetection analysis. The samples include, but are not limited to, a mixture of a chemical molecule, a peptide molecule, a protein molecule, an RNA molecule, a DNA molecule, a traditional antibody, e.g., two heavy chains and two light chains, a recombinant antibody or fragment, a bacterial cell, a virus particle, a cell, a particle, and a product comprising crosslinking any two or more of the above.

Those skilled in the art will know how to apply samples to membrane, which includes, but not limits to direct application in Dot blot analysis, gel electrophoresis and blot transfer in Western blot analysis, and coating of multiwell plates in ELISA assay.

Those skills in the art will know how to block the membrane, which includes, but not limited to using blocking buffer consisting of 5% non-fat milk, or 2% BSA in either PBS or TBS buffer supplemented with 0.1% Tween 20. There are variations of the concentration and substitutes of above reagents known in the art.

Those skills in the art will know how to incubate the antibody with prepared samples. While conventional method include steps of incubation of primary antibody, wash and incubation of secondary antibody with membrane, there are known variations among these steps, yet, not departing from the broad inventive concept of current invention.

Those skills in the art will know how to detect the results in conventional immunodetection analysis. There are multiple methods to either directly label the primary antibody, or indirectly label the secondary antibody to give readout of the amount of the bound immunocomplex on membrane in the detection process. For example, enzymatic coupling of the antibody, radiolabeling with antibody, or labeling the antibody with fluorescent dye, and the readout can be detected either through visual inspection in a color reaction, or through X-ray film when antibody is labeled with radioactive materials. While these variations are extensive, they are not departing from the broad inventive concept of current invention.

In this invention, an additional elution step is included in the conventional immunodetection analysis, between the blocking/incubation/washing step and detection step, as demonstrated in FIG. 2. The membrane-bound antigen-antibody immunocomplex formed in the blocking/incubation/washing step is exposed to excessive amount of antigen, either in single copy or in multiple copies in a single molecule, in elution buffer. The reporter enzyme-labeled antibody, freed from antigen-antibody immunocomplex, is released into elution buffer from membrane. In the detection step, reporter assay is initiated in the elution buffer rather than on the surface of the membrane, allowing for direct quantification of the readout of the reporter assay.

By including an elution step in the otherwise conventional immunodetection process, this invention improves specificity of the Dot blot analysis, allowing the result to be directly quantifiable. Moreover, This invention preserves the advantage of the Dot blot analysis of being fast and simple, allowing for its large-scale applications and in multiwell plate format.

Furthermore, this invention provides an additional advantage over the conventional immunodetection process. In conventional immunodetection analysis, the signal readout is "on the spot", in other word, the immunocomplex being detected remains bound to the membrane through its tight association with the bound antigen of interest. A deviation of this invention from conventional immunodetection analysis is that the labeled antibody is freed from the immunocomplex bound on the membrane into the elution solution to avoid any possible physical limitation of the membrane in the detection process. For example, a common practice of immunodetection in both Dot blot and Western blot analyses is to label the antibody with horseradish peroxidase, which converts ECL substrate into chemiluminescent signals "on the spot" of the membrane. The chemiluminescent signal intensity is manifested with the help of a chemiluminescence sensitive film, and quantified indirectly through densitometric analysis. The overall process is complicate and inaccurate in nature. Current invention, on the other hand, eliminates the need of film and densitometer in this process to quantify freed antibody labeled with horseradish peroxidase directly in elution buffer using microplate luminometer. While this specific example merely serves to illustrate the advantage of current invention, it needs to be understood that the invention is not limited thereto.

Furthermore, the invention also retains the advantage of the ELISA assay while loosens its demand on the specificity of the antibody. The inclusion of an excessive amount of the antigen of interest in the elution step allows only those antibodies bound to the antigen of interest being liberated from the membrane, preventing any interference from non-specific interactions commonly observed with a large number of antibodies used in current biological research. Therefore, the availability of the suitable antibodies for immunodetection in multiwell plate format increases significantly as a result of this invention.

As used herein 'membrane" is to be taken in its broadest context. A membrane can be any material with sufficient surface porosity to allow access by detection antibodies and a suitable surface affinity to bind antigen. All these materials may be used in suitable shapes, such as films, sheets, or plates; or, they maybe coated onto or bonded or laminated to appropriate insert carriers, such as paper, glass, plastic materials or fabrics. For example, a membrane can be, but not limited to, nitrocellulose membrane, PVDF membrane, or multiwell plate in ELISA assay.

As used herein 'reporter enzyme' is to be taken in its broadest context. A reporter enzyme can be any modification of the antibody in immunodetection assay with the purpose to aid the detection of the antibody. For example, a reporter enzyme can be, but not limited to, antibody directly labeled with radioactive isotope like Iodide 125, or reporter enzymes like alkaline phosphatase or horseradish peroxidase. The detection of the amount of reporter enzymes associated with antibody is through the formation of a detectable product as the readout of the amount of reporter enzymes in the detection reaction. The product can be radioactive, luminescent, fluorescent, or a product with characteristic absorbance or reflection spectrum in the visible or outside the visible range. When a complement is used to detect the bound antigen-antibody complex, it may either be labeled in any one of the above ways, or be detected in turn by a specific anti-complement antibody.

As used herein 'antigen" and an "antibody" are to be taken in their broadest context. An "antigen" can be any molecule, cell, virus, or particle. For example, an antigen includes, but is not limited to, a chemical molecule, a peptide molecule, a protein molecule, an RNA molecule, a DNA molecule, a traditional antibody, e.g., two heavy chains and two light chains, a recombinant antibody or fragment, a bacterial cell, a virus particle, a cell, a particle, and a product comprising crosslinking any two or more of the above. An antigen can exists either in a pure form, or it can exist in a mixture. An antigen can be in a modified form (e.g., modified by a chemicals) or be in an unmodified form.

Reference herein to an "antibody" is to be taken in its broadest context. "An antibody" is a polypeptide that binds to "an antigen". An antibody includes, but is not limited to, a traditional antibody, a fragment of a traditional antibody containing an antigen binding site, a recombinant antibody containing an antigen binding site, a protein which binds to an antigen, and a product that comprises of crosslinking any two or more of the above. An antibody can exists either in a pure form, or in a mixture. An antibody can be in a modified form (e.g., modified by a chemical) or be an unmodified form.

Reference herein to an 'elution step' is to be taken in its broadest context. 'Elution' is to free an antibody labeled directly, or indirectly through a secondary antibody with a reporter enzyme, from a bound immunocomplex containing the antigen of interest on the membrane using an excessive amount of antigen or any molecule sharing the same binding site or sites of the antibody with the antigen of interest. It also includes, but is not limited to, molecule that does not share the same binding site of the antibody, but can disrupt the bound immunocomplex on the membrane while maintain the specificity of the immunodetection process. The excessive antigen can exist in single copy, or in multiple repeats in a single molecule for this purpose.

An antigen in "elution step" in this invention is to be taken in its broadest context. Antigen can be the complete molecule of the antigen, or part of the antigen of interest if this part of the molecule is known to be able to compete with the antigen of interest in the bound antigen-antibody immunocomplex.

The antigen or part of the antigen may carry one or multiple epitopes. In the case where the epitope against a specific antibody is known, an antigen here can be the epitope peptide in single or multiple copies.

In one aspect, the invention provides an improved Dot blot analysis with modifications. The process begins with the direct application of prepared samples containing antigen of interest to membrane, preferably in a multiwell plate format. The non-specific protein binding site on the membrane is blocked, followed by the addition of the antibody labeled directly with reporter enzyme, or the addition of primary antibody followed by the secondary antibody labeled with reporter enzyme after successive washes. Unbound antibodies are washed away in the wash buffer without interfering with the established antigen-antibody interaction. The bound antibodies on the membrane, through antigen-antibody interaction, are eluted with solution containing an excessive amount of the antigen of interest (single copy or multiple copies in a single molecule). The amount of liberated antibody labeled with reporter enzyme is measured directly in the elution solution through formation of reporter enzyme-mediated product, without the necessity of a medium, such as X-ray film.

In one aspect, the invention is to simplify the conventional Western blot analysis technique by eliminating both the gel electrophoresis and blot transfer steps to allow for large-scale analysis of protein samples in experimental, clinical and pharmaceutical settings. The results of the protein analysis can also be directly quantified, thus eliminating the inherent inaccuracy associated with the conventional methods.

The intention of the invention is also to simplify the complicated developmental process associated with the ELISA assay. The current invention, with the inclusion of increased dosage of antigen of interest as standard, can easily be translated into an ELISA assay with the same accuracy yet increased availability of suitable antibodies.

The intention of this invention is also to increase the efficiency of conventional protein analysis techniques. The process begins with direct application of prepared samples containing multiple antigens of interest onto the membrane, and following a blocking step and the incubation of the membrane with a mixture of antibodies against each individual antigen of interest simultaneously. The addition of elution step in this invention allows for the liberation of individual antibody (directly or indirectly labeled with reporter enzyme) from its very bound immunocomplex using elution solution containing an excessive amount of antigen specific for the very antibody without interfering with bound immunocomplexes of other antibodies and their respective antigens of interest. Direct quantification of the amount of reporter enzyme coupled with individual antibody in elution buffer determines the amount of antigen of interest in prepared sample. Repeated elution steps using each individual antigen lead to the quantification of every antigen of interest in prepared sample stepwise in a short time span.

The intention of this invention is also to be used in protein microarray analysis. The process begins with the application of prepared samples in a multiwell plate format. The bound multiwell plate with antigens of interest is blocked to eliminate any non-specific protein binding sites, followed by simultaneous incubation with multiple antibodies labeled directly or indirectly with reporter enzyme. The multiwell plate is to be loaded with elution buffer, with each well holding an excessive amount of different antigen of multiple antigens of interest to be examined, and the incubation of the elution buffer liberates its matching antibody from bound immunocomplex in each well of the multiwell plate. The elution buffer is separated from the solid phase of the multiwell plate, and quantified of the relative amount of different antigen of interest in each well through reporter enzyme-mediated reaction simultaneously.

The simplicity of the process is also to be used in automated process. Compared with conventional methods, the steps necessary for immunodetection analysis in this invention are limited to incubation and changing of different solutions, thus simplifying the overall process significantly, allowing for large-scale automated process in clinical, experimental, and pharmaceutical research and for diagnostics purpose.

It will be appreciated by those skilled in the art that changes could be made to the embodiments described above without departing from the broad inventive concept thereof. It is understood, therefore, that this invention is not limited to the particular embodiments disclosed, but is intended to exemplify modifications that are within the spirit and scope of the invention, as defined by the appended claims.

The following example of the method of the invention is to further illustrate of the nature of the invention. It needs to be understood that the invention is not limited thereto.

EXAMPLE

Improved Zestern method of analysis of FLAG-tagged IRS-2 protein expression in HEK-293 cells.

HEK-293 cells were transfected using Fugene 6 method of 2 μg/60 mmdish of FLAG-tagged IRS-2 construct. After 48 hours of transfection, total cell lysates were prepared in lysis buffers containing protease inhibitors (Zhang, J., 2007). Total cell lysates were resuspended in 4×SDS sample buffer (Laemmli buffer), and heated 5 mins at 75° C. before they were applied to the individual units of PVDF membrane following standard Dot blot procedure. These individual units of PVDF membrane were blocked with blocking buffer (5% milk in Tris buffered saline supplemented with 0.1% of Tween 20, TBST) for 1 hour before they were exposed to M2 FLAG antibody (Sigma, St. Louis) in blocking buffer at 1:1000 dilution for 2 hours, followed by 3×5 mins wash of TBST buffer, and 2 hours of incubation in Donkey anti-mouse secondary antibody at 1:5000 dilution. After another 3×5 mins of wash with TBST buffer, these individual units of PVDF membrane were incubated with 100 μl of elution solution (1×PBS containing 3×FLAG peptide (Sigma, St. Louis, Mo.) at final concentration of 150 ng/μl) for another 1 hours to elute bound antibodies (primary antibody bound with reporter enzyme-labeled secondary antibody) from individual unit of PVDF membrane). The elution solution of 50 μl was transferred to a 96 well black flat bottom plate, and mixed with 50 μl of prepared ECL solution (GE healthcare) before it was quantified in a standard luminometer.

The luminometer readings (arbitrary unit):

| | |
|---|---|
| Blank | 98 +/− 5 |
| Total cell lysates from Mock transfected cells Eluted with 3XFLAG peptide | 211 +/− 20 |
| Total cell lysate from cells transfected with FLAG-IRS-2, eluted with 3X FLAG peptide | 34023 +/− 3265 |
| Total cell lysates from cells transfected with FLAG-IRS-2, eluted with TBS alone | 1041 +/− 130 |

The result is the average of three repeats in duplicate

The result is the average of three repeats in duplicate

The invention claimed is:

1. An improved method of immunodetection process of an antigen of interest in a sample, wherein the process comprises the steps of:
   a) applying said sample containing said antigen to bind said antigen onto a solid phase;
   b) blocking said solid phase to eliminate non-specific antibody binding to said solid phase;
   c) incubating said solid phase with a primary antibody that is specific for said antigen, and which is labeled, directly or indirectly through a secondary antibody, with reporter enzymes, to form an antigen-antibody immunocomplex;
   d) eluting said solid phase with a solution containing excess of free said antigen or any polypeptide, which is capable of disrupting said antigen-antibody immunocomplex through competition, in order to liberate said primary antibody, directly or indirectly labeled with reporter enzymes, from said immunocomplex;
   e) collecting the eluates and quantifying said bound antigen of step a) by quantifying said liberated primary antibody in a reporter assay.

2. The method of claim 1, wherein the solid phase is a membrane, or multiwell plate, or any material with sufficient surface porosity to allow access by detection antibodies and a suitable surface with affinity to bind antigen, wherein said solid phase is used in suitable shapes, wherein said solid phase is selected from the group consisting of films, sheets, plates, paper, glass, plastic and fabrics.

3. The method of claim 1, wherein the solid phase comprises an ELISA plate.

4. The method of claim 1, wherein the antigen is selected from the group consisting of a polypeptide, a chemical, an RNA, a DNA, a cell, and a virus particle.

5. The method of claim 4, wherein the polypeptide is an antibody.

6. The method of claim 1, wherein the elution solution contains excess of free said antigen in single or multiples copies within one molecule to liberate the labeled antibody from the immunocomplex bound to the solid phase.

7. The method of claim 1, wherein the eluting solution contains a whole antigen, or only the antibody-interacting region of the antigen, in single or multiple copies within one molecule.

8. The method of claim 7, wherein the eluting solution contains epitope peptide in a single or multiple copies within a molecule.

9. The method of claim 1, wherein the reporter enzyme can be detected by radiolabeling, infrared labeling or fluorescence-labeling.

10. The method of claim 1, wherein the quantification includes a step of separating eluting solution containing liberated antibody labeled with reporter enzyme from said solid phase.

11. The method of claim 1, wherein the process is conducted in an automated assay.

12. The method of claim 1, wherein different antigens of interest can be measured simultaneously in a multiwell format in a protein microarray assay, wherein each individual antigen is bound unto an individual well on said microarray for analysis.

13. The method of claim 1, wherein said solid phase is incubated with a mixture of antigen-specific primary antibodies to form a mixture of antigen-antibody immunocomplexes, wherein said primary antibodies are each labeled, directly or indirectly through secondary antibodies, with reporter enzymes; and eluting said solid phase repeatedly with solution containing excess of each free individual antigen or any polypeptide, which is capable of disrupting each individual antigen-antibody immunocomplex through competition, in order to liberate each individual primary antibody from said immunocomplexes for quantification.

14. The method of claim 1, wherein the eluting solution contains polypeptides with stronger binding affinity than the said antigen of interest.

* * * * *